US012576193B2

(12) United States Patent
Chen

(10) Patent No.: US 12,576,193 B2
(45) Date of Patent: Mar. 17, 2026

(54) BREAST PUMP

(71) Applicant: SHENZHENSHI LUTEJIACHENG SUPPLYCHAIN MANAGEMENT CO., LTD., Shenzhen (CN)

(72) Inventor: Wanyuan Chen, Shenzhen (CN)

( * ) Notice: Subject to any disclaimer, the term of this patent is extended or adjusted under 35 U.S.C. 154(b) by 0 days.

(21) Appl. No.: 17/962,556

(22) Filed: Oct. 10, 2022

(65) Prior Publication Data

US 2024/0001008 A1      Jan. 4, 2024

(30) Foreign Application Priority Data

Jul. 4, 2022    (CN) .......................... 202221735508.2

(51) Int. Cl.
A61M 1/06            (2006.01)
(52) U.S. Cl.
CPC ......... A61M 1/062 (2014.02); *A61M 2205/82* (2013.01)
(58) Field of Classification Search
CPC ............................................. A61M 1/06–0697
See application file for complete search history.

(56) References Cited

U.S. PATENT DOCUMENTS

| | | |
|---|---|---|
| 8,118,772 B2 | 2/2012 | Dao et al. |
| 11,090,418 B2 | 8/2021 | Hwang |
| 11,541,156 B2 | 1/2023 | Hwang |
| 11,554,198 B1 | 1/2023 | Pan |
| 11,554,199 B1 | 1/2023 | Chen |

| | | |
|---|---|---|
| 11,806,454 B2 | 11/2023 | De Becdelievre et al. |
| 2007/0159772 A1* | 7/2007 | Morice .................. H01R 13/60 |
| | | 361/600 |
| 2014/0094748 A1 | 4/2014 | Hong et al. |
| 2015/0217034 A1 | 8/2015 | Pollen |
| 2016/0296682 A1 | 10/2016 | Phillips et al. |
| 2017/0216505 A1 | 8/2017 | Kim |

(Continued)

FOREIGN PATENT DOCUMENTS

EP            3777911 A1      2/2021

*Primary Examiner* — Courtney B Fredrickson

(57) ABSTRACT

A breast pump relating to the technical filed of breast pumps is provided, comprising a base, a breast pump assembly and a ventilation tube. The base includes a housing and a pneumatic pump, and the pneumatic pump is arranged in the housing. The breast pump assembly is used for pumping the milk of the mammary gland, and is detachably connected to the housing. When the breast pump assembly is separated from the housing, the ventilation tube is connected to the pneumatic pump and the breast pump assembly, so that the pneumatic pump forms a negative pressure on the breast pump assembly. The breast pump assembly is connected to the housing when the ventilation tube is disconnected from the pneumatic pump and the breast pump assembly. The base included in the above breast pump assembly is detachably connected to the breast pump assembly. When it needs to be used separately, the base and the breast pump assembly is disassembled and separated first, and then the ventilation tube is connected to the pneumatic pump and the breast pump assembly. When it is not required to be used separately, the ventilation tube is disassembled and the breast pump assembly can be connected to the base. The breast pump has strong compatibility, can meet the various needs of users, and has a good user experience.

9 Claims, 6 Drawing Sheets

(56)         References Cited

U.S. PATENT DOCUMENTS

| 2020/0384172 | A1* | 12/2020 | Kim .................... A61M 1/0697 |
|---|---|---|---|
| 2021/0228789 | A1 | 7/2021 | O'Toole et al. |
| 2021/0252202 | A1* | 8/2021 | Kim .................... A61M 1/0697 |
| 2022/0265907 | A1* | 8/2022 | Hwang ................ A61M 1/067 |
| 2023/0111110 | A1* | 4/2023 | De Becdelievre ...... A61M 1/60 |
| | | | 604/74 |
| 2023/0211056 | A1* | 7/2023 | Mou .................... A61M 1/066 |
| | | | 604/74 |

* cited by examiner

100

2

1

100

2

3

114

1

1123

114

2

BREAST PUMP

FIELD OF THE DISCLOSURE

The present disclosure relates to the technical field of breast pumps, in particular, to a breast pump.

BACKGROUND OF THE DISCLOSURE

The breast pump is used to assist breastfeeding women to pump out the milk from the mammary glands and store it in a feeding bottle to solve the problem of breastfeeding in breastfeeding women. The breast pump is mainly composed of a fixed seat and a breast pump. The pneumatic pump in the fixed seat can provide negative pressure for the breast pump, so that the breast pump can suck the milk in the mammary gland. However, the existing breast pump either has an integral structure of the fixed seat and the breast pump cover, which cannot be disassembled and used separately; or the fixed seat and the breast pump cover are used separately but cannot be installed and connected together, resulting in poor compatibility and poor user experience.

SUMMARY OF THE DISCLOSURE

Based on this, it is necessary to solve the problem of poor compatibility between the fixed seat of the breast pump and the breast pump cap, and poor user experience.

The present disclosure is to provide a breast pump, comprising: a base including a housing and a pneumatic pump, wherein the pneumatic pump is arranged in the housing; a breast pump assembly for pumping milk from mammary glands, and being detachably connected to the housing; and a ventilation tube, wherein when the breast pump assembly is separated from the housing, the ventilation tube is correspondingly connected to the pneumatic pump and the breast pump assembly, so that the pneumatic pump forms a negative pressure on the breast pumping assembly; wherein when the ventilation tube is disengaged from the pneumatic pump and the breast pump assembly, the breast pump assembly is connectable to the housing.

The base included in the above breast pump is detachably connected to the breast pump assembly. When it needs to be used separately, the base and the breast pump assembly can be disassembled and separated first, and then the ventilation tube is connected to the pneumatic pump and the breast pump assembly. When it is not required to be used separately, the ventilation tube can be disassembled and the breast pump assembly can be connected to the base. The breast pump has strong compatibility, can meet the various needs of users, and has a good user experience.

In one of the embodiments, the housing has an insertion post, the breast pump assembly is provided with an insertion hole, and the insertion post and the insertion hole are detachably engaged to each other.

In one of the embodiments, the housing is provided with a positioning groove, the insertion post is arranged in the positioning groove, the breast pump assembly has a positioning flange, the insertion hole is arranged in the positioning flange, and when the insertion post is engaged to the insertion hole, the positioning flange is engaged to the positioning groove.

In one of the embodiments, one of the housing and the breast pump assembly has a connecting post, another one of the housing and the breast pump assembly is provided with a connecting groove, and the connecting post and the connecting groove are detachably engaged to each other;

wherein when the connecting post is engaged to the connecting groove, the pneumatic pump communicates with the breast pump assembly; wherein when the connecting post is separated from the connecting groove, two ends of the ventilation tube are respectively connected to the connecting post and the connecting groove, so that the pneumatic pump is connected to the breast pump assembly through the ventilation tube.

In one of the embodiments, the housing has a first surface, the breast pump assembly has a second surface, the first surface and a thickness direction of the base are arranged at an angle to each other, and when the breast pump assembly is connected to the housing, the first surface is in contact with the second surface.

In one of the embodiments, the base further comprises a mounting member provided on the housing, and the mounting member is configured to be detachably worn on a user.

In one of the embodiments, the housing is provided with a movable groove that is hollow, so that a mounting cross rod is arranged on the housing, and the mounting member is sleeved on the mounting cross rod and is able to rotate in the movable groove.

In one of the embodiments, the mounting member has a first section, a second section and a third section, the first section and the third section respectively are arranged on opposite sides in a thickness direction of the second section, the first section is curved to be sleeved on the mounting cross rod, and the third section is curved to be detachably fastened to the user.

In one of the embodiments, the breast pump assembly has a milk holding cavity and the milk holding cavity is used to hold pumped milk.

In one of the embodiments, the base further comprises a mobile power supply provided in the housing, and the mobile power supply is used for supplying power to the pneumatic pump, so that the pneumatic pump forms the negative pressure on the breast pump assembly.

In the accompanying drawings, the list of components represented by each number is as follows.

100. breast pump; 1. base; 11. housing; 111, upper half shell; 1111. buckle; 1112. through hole; 1113. first surface; 1114. positioning groove; 1115. insertion post; 1116. movable groove; 1117. mounting cross rod; 112, lower half shell; 1121. clip slot; 1122. charging hole; 1123. dust plug; 1124. switch key; 1125. mode key; 1126. gear increase key; 1127.

gear reduce key; 113. bottom shell; 1131. hook; 114. mounting member; 1141. first section; 1142. second section; 1143. third section; 12. circuit board; 121. charging part; 13. pneumatic pump; 14. solenoid valve; 15. three-way connector; 151. connecting groove; 16. battery; 2. breast pump assembly; 21. storage member; 211. accommodating cavity; 212. capacity scale; 213. second surface; 214. connecting post; 215. positioning flange; 216. insertion hole; 217. clip flange; 218. third surface; 22. adapter; 221. adapter housing; 2211. air pressure housing; 2212, tube body; 222 air pressure elastic member; 223 milk release member; 2231 connecting head; 2232 one-way head; 224 first air pressure chamber; 225 second air pressure chamber; 23. face cover; 231. socket; 232. sealing ring; 233. mounting groove; 234. liquid inlet groove; 3. ventilation tube

DETAILED DESCRIPTION OF THE EXEMPLARY EMBODIMENTS

In order to make the above-mentioned objects, features and advantages of the present disclosure more obvious and easy to understand, the specific embodiments of the present disclosure will be described clearly and completely below with reference to the accompanying drawings. Obviously, the in specific details described below are only a part of the embodiments of the present disclosure, and the present disclosure can also be implemented in many other embodiments different from those described herein. Based on the embodiments of the present disclosure, all other embodiments obtained by those of ordinary skill in the art without creative work all belong to the protection scope of the present disclosure.

It should be noted that when an element is referred to as being "fixed to" another element, it can be directly on the other element or intervening elements may also be present. When an element is referred to as being "connected" to another element, it can be directly connected to the other element or intervening elements may also be present. The terms "vertical", "horizontal", "left", "right" and similar expressions used herein are for the purpose of illustration only and do not represent the only embodiment.

Unless otherwise defined, all technical and scientific terms used herein have the same meaning as commonly understood by one of ordinary skill in the technical field to which the present disclosure belongs. The terms used in the description of the present disclosure herein are only for the purpose of describing specific embodiments, and are not intended to limit the present disclosure.

Figure 1:
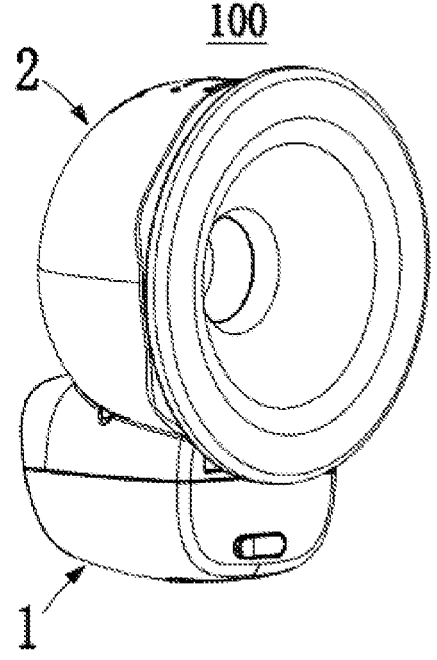
FIG. 1 is a schematic structural diagram of the breast pump when the breast pump of the present disclosure is in a combined state.
Figure 2:
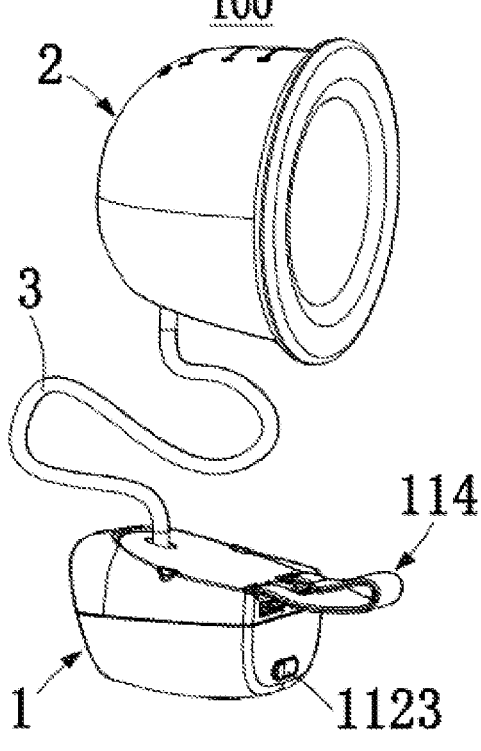
FIG. 2 is a schematic structural diagram of the breast pump from a perspective when the breast pump of the present disclosure is in a separate state.

Referring to FIG. 1 and FIG. 2, the present disclosure provides a breast pump 100, which is used to assist breast-feeding women to suck out and store milk in their mammary glands, which is convenient for breastfeeding women.

The breast pump 100 includes a base 1, a breast pump assembly 2 and a ventilation tube 3. Both ends of the ventilation tube 3 are detachably connected to the base 1 and the breast pump assembly 2, and the base 1 can be detachably connected to the breast pump assembly 2.

Figure 3:
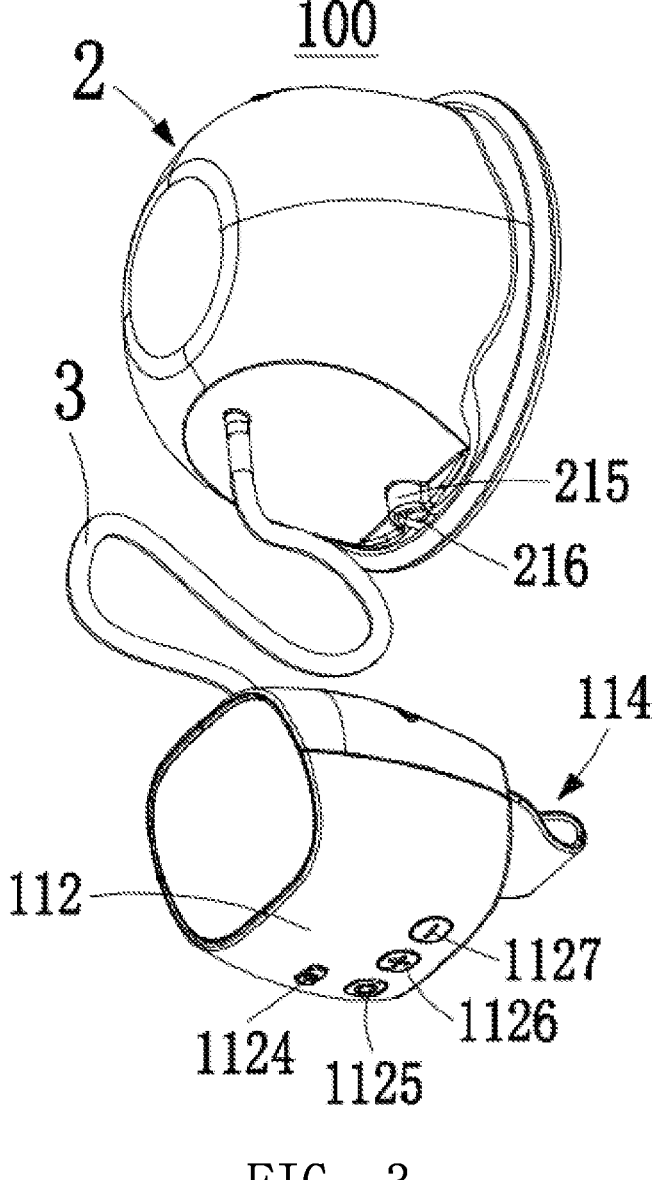
FIG. 3 is a schematic structural diagram of the breast pump from a perspective when the breast pump of the present disclosure is in a combined state.
Figure 4:
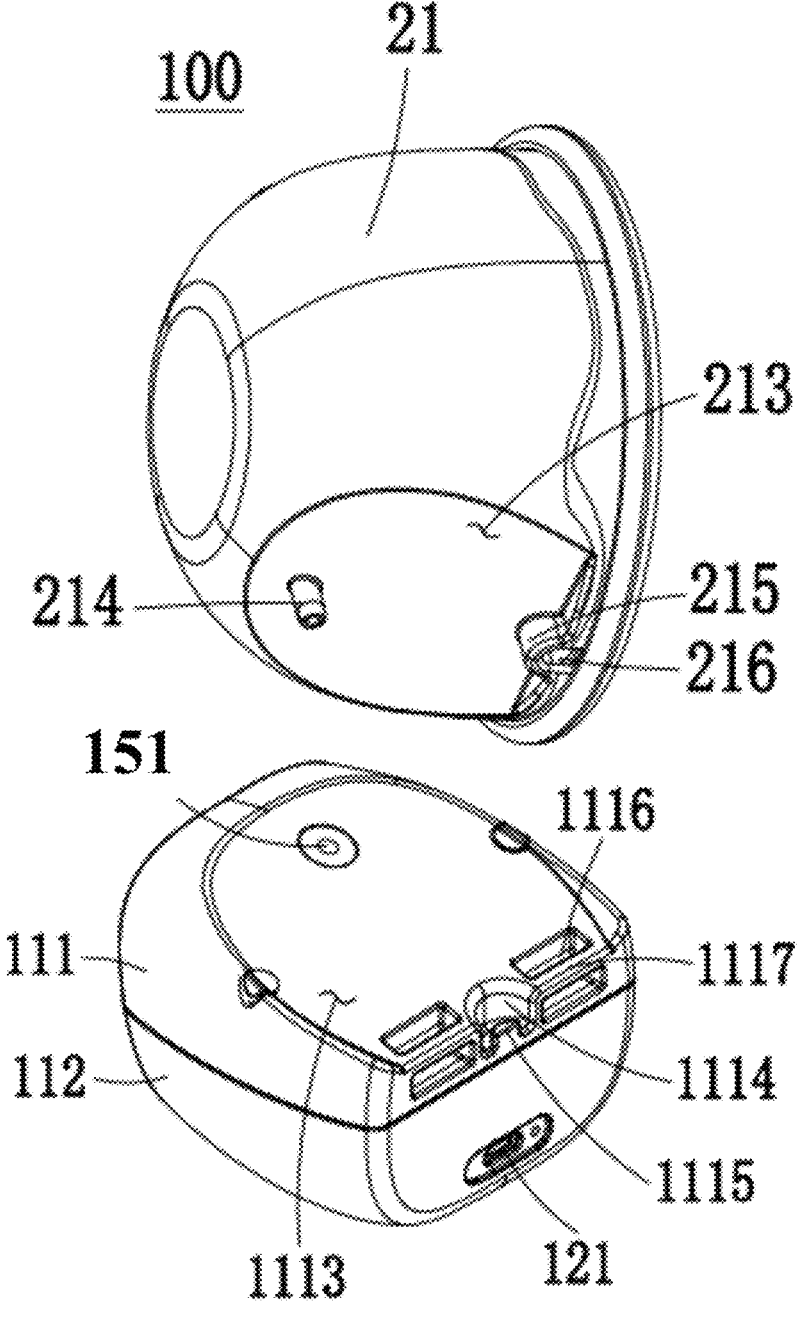
FIG. 4 is a schematic diagram of the exploded structure of the breast pump of the present disclosure.

The breast pump 100 mainly has two usage states, the breast pump 100 shown in FIG. 1 is in a combined state, and the breast pump 100 shown in FIGS. 2 and 3 is in a separate state.

The base 1 of the breast pump 100 in the combined state is in a connected state with the breast pump assembly 2. The breast pump in this state does not need to use a ventilation tube. After the base 1 is connected to the breast pump assembly 2, the base 1 can directly form a negative pressure on the breast pump assembly 2, so that the breast pump assembly 2 can pump milk to the mammary glands. The breast pump 100 in this state can stabilize the breast pump assembly 2. For example, after the breast pump assembly 2 completes pumping milk, the milk is stored in the breast pump assembly 2. In order to prevent the milk from leaking easily, the ventilation tube 3 can be disassembled first, and then the base 1 and the breast pump assembly 2 are connected. The base 1 can support the breast pump assembly 2 and prevent the breast pump assembly 2 from being easily overturned.

In the separate state, the base 1 of the breast pump 100 is in a separate state from the breast pump assembly 2, and the base 1 communicates with the breast pump assembly 2 through the ventilation tube 3. The breast pump assembly 2 can be placed on the breast, the base 1 can be worn on the user's waist or head, etc., and the base 1 can form a negative pressure on the breast pump assembly 2 through the ventilation tube 3, so that the breast pump assembly 2 can pump milk to the breast. Compared with the breast pump in which the base 1 and the breast pump assembly 2 are not detachable, the breast pump 100 in the separate state of the present disclosure can prevent the weight of the base 1 from being loaded on the breast pumping assembly 2 and easily make the breast pumping assembly 2 detach from the mammary glands, thereby affecting the pumping of milk.

Therefore, the user can selectively switch the breast pump 100 between the separate state and the combined state according to their actual situation. The breast pump 100 is highly compatible in use and has a good user experience.

Referring to 4 and 5, the base 1 includes a housing 11, a circuit board 12, a pneumatic pump 13, a solenoid valve 14, a three-way connector 15 and a battery 16 arranged inside the housing 11. The pneumatic pump 13, the solenoid valve 14 and the battery 16 are connected to the circuit board 12, and the three-way connector 15 is connected to the solenoid valve 14 and the pneumatic pump 13.

The housing 11 includes an upper half shell 111, a lower half shell 112, a bottom shell 113 and a mounting member 114. The upper half shell 111 and the lower half shell 112 are detachably connected to each other, and the bottom shell 113 is detachably connected to the upper half shell 111 and the lower half shell 112. The lower half shell 112 is connected to the upper half shell 111 by the mounting member 114.

The opposite parts of the upper half shell 111 and the lower half shell 112 are hollow, so that after the upper half shell 111 and the lower half shell 112 are connected, other components such as the pneumatic pump 13 can be accommodated.

The side of the upper half shell 111 facing the lower half shell 112 is provided with a plurality of buckles 1111 along the circumferential direction, and each buckle 1111 is used for detachably clipping to the lower half shell 112.

The upper half shell 111 is provided with a through hole 1112 along its thickness direction, and the through hole 1112 can be used for the three-way connector 15 to protrude from the inside of the upper half shell 111 to the outside, so that the three-way connector 15 can be connected with the breast pump assembly 2, and then the pneumatic pump 13 evacuates or pressurizes the breast pump assembly 2 through the three-way connector 15.

A first surface 1113 is disposed on the side of the upper half shell 111 facing away from the lower half shell 112, and the first surface 1113 and the thickness direction of the upper half shell 111 are arranged at an angle. Compared with the non-inclined surface, the inclined first surface 1113 can increase the contact area with the breast pump assembly 2. When the breast pump assembly 2 is connected to the upper half shell 111, the upper half shell 111 can provide a larger support surface for the breast pump assembly 2, so as to support the breast pump assembly 2 stably.

The upper half shell 111 is provided with a positioning groove 1114, and the positioning groove 1114 can be mated and inserted with the breast pump assembly 2 to position the breast pump assembly 2, so that the breast pump assembly 2 can be installed more stably on the upper half shell 111.

The upper half shell 111 also has an insertion post 1115 disposed at the bottom of the positioning groove 1114, and the insertion post 1115 is used for detachably inserting the breast pump assembly 2 to install the breast pump assembly 2. When the insertion post 1115 is inserted into the breast pump assembly 2, the breast pump assembly 2 is also located in the positioning groove 1114. The double function of the insertion post 1115 and the positioning groove 1114 enables the breast pump assembly 2 to be installed more stably on the upper half shell 111.

The upper half shell 111 is provided with a hollow movable groove 1116, and the movable groove 1116 is formed with a mounting cross rod 1117 on the housing, and the mounting cross rod 1117 is used for the mounting member 114 to be detachably socketed. When the mounting member 114 is sleeved on the mounting cross rod 1117, the mounting member 114 can be rotated in the movable groove 1116 to facilitate the wearing of the mounting member 114. The mounting member 114 can be worn on the user's body, such as the waist, the head, etc., so that the entire base 1 is fixed on the user's body through the mounting member 114.

The base 1 of the breast pump 100 in the detached state can be fixed on the user's waist through the mounting member 114, and the breast pump assembly 2 can be placed on the user's breast. The breast pump assembly 2 is connected to the base 1 through the ventilation tube 3, and the pneumatic pump 13 in the base 1 can vacuum the breast pump assembly 2, so that the breast pump assembly 2 can pump the milk in the mammary glands. The user does not need to fix the breast pump assembly 2 by hand, and can place the breast pump assembly 2 inside the underwear to fix the breast pump assembly 2 on the mammary glands and free the user's hands, and the user can pump breast while moving so as to have good user experiences.

Referring to 5 and 6, the mounting member 114 includes a first section 1141, a second section 1142 and a third section 1143. The first section 1141 and the third section 1143 are provided on opposite sides of the second section 1142 in the thickness direction. Both the first section 1141 and the third section 1143 are curved, and both are curved toward the middle of the second section 1142. The curved first section 1141 is used to be sleeved on the mounting cross rod 1117, and the curved third section 1143 can be detachably fastened to the user, for example, to the user's belt. Alternatively, the third section 1143 is connected to a strap that is tied around the user's waist or other parts.

The mounting member 114 can be made of hard plastic, so that the mounting member 114 is light in weight, and the first section 1141 is easy to disassemble and assemble on the mounting cross rod 1117, and the third section 1143 is easy to disassemble and assemble on the belt.

The lower half shell 112 is provided with a clip slot 1121, and the clip slot 1121 is used for detachably clipping with the buckle 1111 of the upper half shell 111. Of course, in other embodiments, the positions of the clip slot 1121 of the lower half shell 112 and the buckle 1111 of the upper half shell 111 can be interchanged, and the upper half shell 111 and the lower half shell 112 can also be detachably clipped together.

The lower half shell 112 is provided with a charging hole 1122, and the charging hole 1122 is used for the charging member 121 on the circuit board 12 to penetrate and extend, so as to be connected to an external power source to charge the battery 16.

The lower half shell 112 is also provided with a dust plug 1123 (shown in FIG. 2), and the dust plug 1123 is used to be inserted into the charging hole 1122. When not charging, the dust plug 1123 can be inserted into the charging hole 1122 to prevent dust from the charging hole 1122 and avoid affecting subsequent charging.

Figure 5:
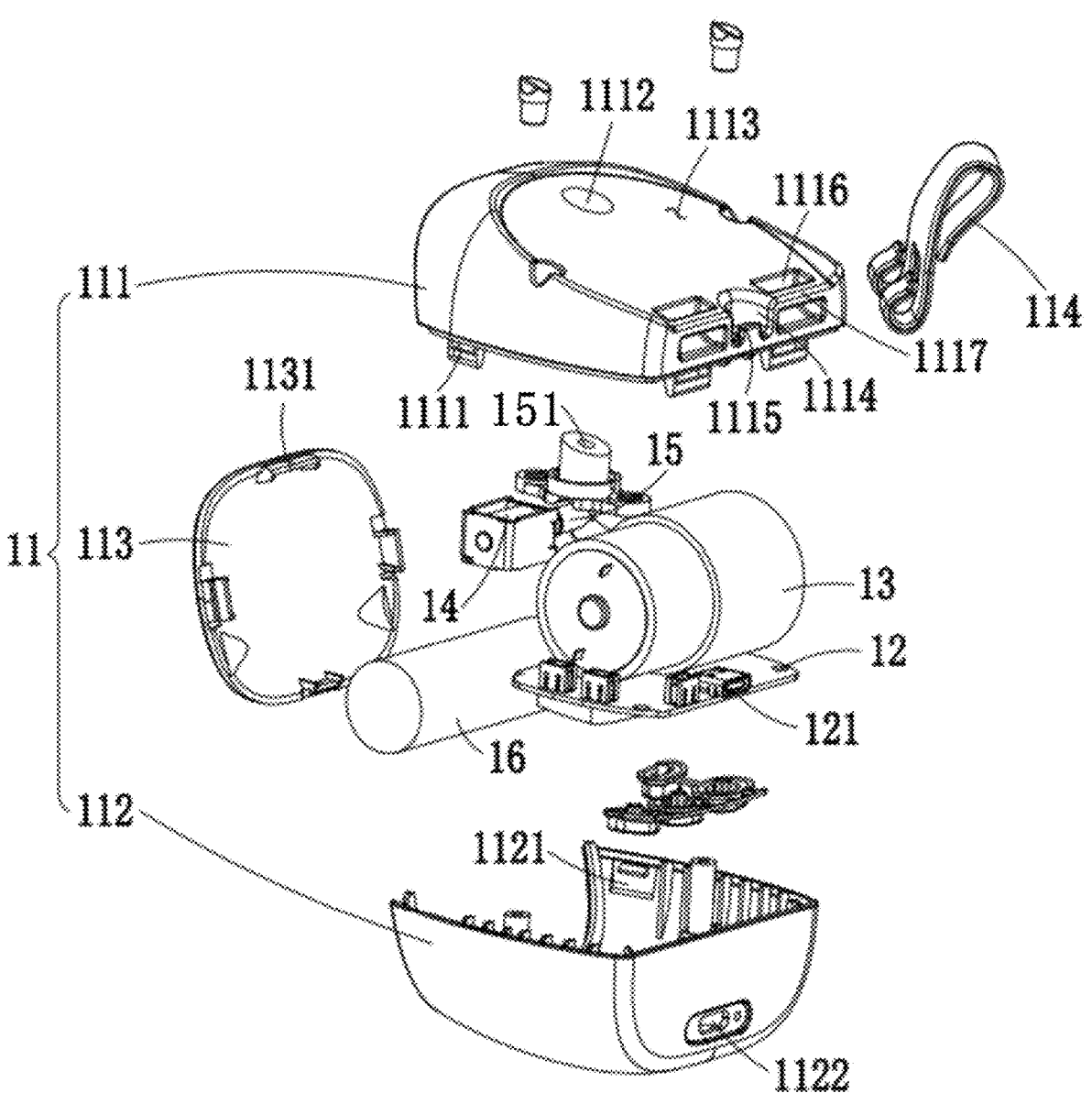
FIG. 5 is a schematic diagram of the disassembled structure of the base of the present disclosure.
Figure 6:
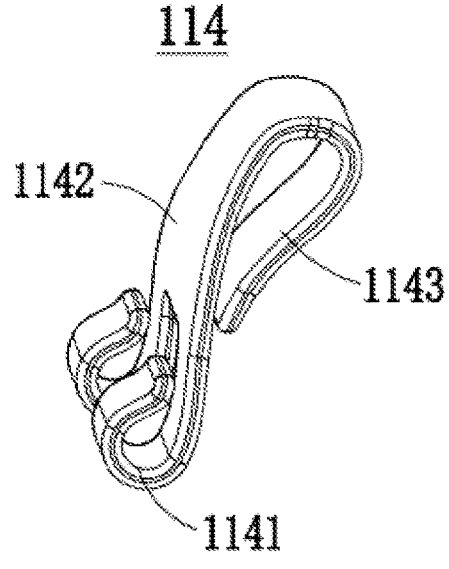
FIG. 6 is a structural schematic diagram of the mounting member of the present disclosure.

Referring to FIGS. 3 and 5, the lower half shell 112 is provided with a plurality of keys connected to the circuit board 12, including a switch key 1124, a mode key 1125, a gear increase key 1126 and a gear reduce key 1127. The switch key 1124 is pressed cyclically, the circuit board 12 can be controlled to be powered on or off, and then the pneumatic pump 13 can be controlled to work or stop. The gear increase key 1126 is used to control the air pressure of the pneumatic pump 13 to increase, so that the vacuuming intensity and the pressing intensity of the pneumatic pump 13 are increased. The gear reduce key 1127 is used to control the reduction of the air pressure of the pneumatic pump 13, so that the vacuuming intensity and the pressing intensity of the pneumatic pump 13 are reduced.

Referring to FIG. 5, the bottom shell 113 is provided with a plurality of hooks 1131 along its circumferential direction, a part of the hooks 1131 is used for detachably clipping the upper half shell 111, and the other part of the hooks 1131 is used for detachably clipping the lower half shell 112 to encapsulate the components inside the housing 11. In addition, when the breast pump assembly 2 is connected to the upper half shell 111, the bottom shell 113 can be attached to a placement surface such as a desktop, so as to assist the breast pump assembly 2 to be fixed on the placement surface such as a desktop.

The three-way connector 15 has a connecting groove 151, and the connecting groove 151 communicates with the pneumatic pump 13. The connecting groove 151 is also used to connect the ventilation tube 3 or directly plug into the breast pump assembly 2, so that the pneumatic pump 13 communicates with the breast pump assembly 2 and then the pneumatic pump 13 vacuums or pressurizes the breast pump assembly 2.

When the three-way connector 15 is installed, a part of the three-way connector 15 is located in the through hole 1112 opened in the upper half shell 111, so that the connecting groove 151 is exposed on the surface of the upper half shell 111, so as to facilitate the insertion of the ventilation tube 3 or the breast pump assembly 2.

The solenoid valve 14 is used to control the pneumatic pump 13 to switch between pumping and inflation. When the pneumatic pump 13 is pumping, the breast pump assembly 2 can be evacuated. When the pneumatic pump 13 is inflated, it can pressurize the breast pump assembly 2. The pneumatic pump 13 alternates between vacuuming and pressurizing the breast pump assembly 2. The vacuuming can pump the milk of the mammary glands. The pumped milk is stored by alternating vacuum and pressurization cycles to gradually extract and store the milk in the mammary glands.

Figure 7:
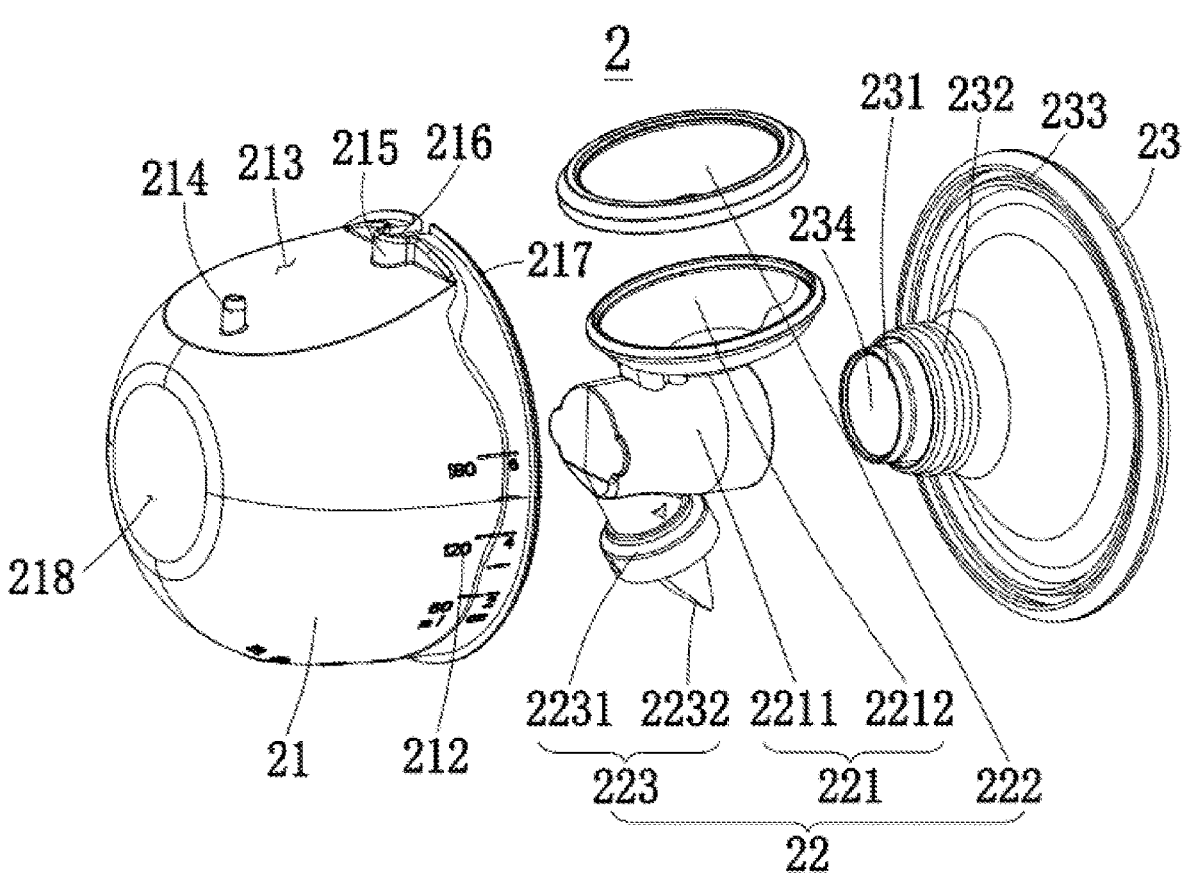
FIG. 7 is a schematic diagram of the disassembled structure of the breast pump assembly of the present disclosure.
Figure 8:
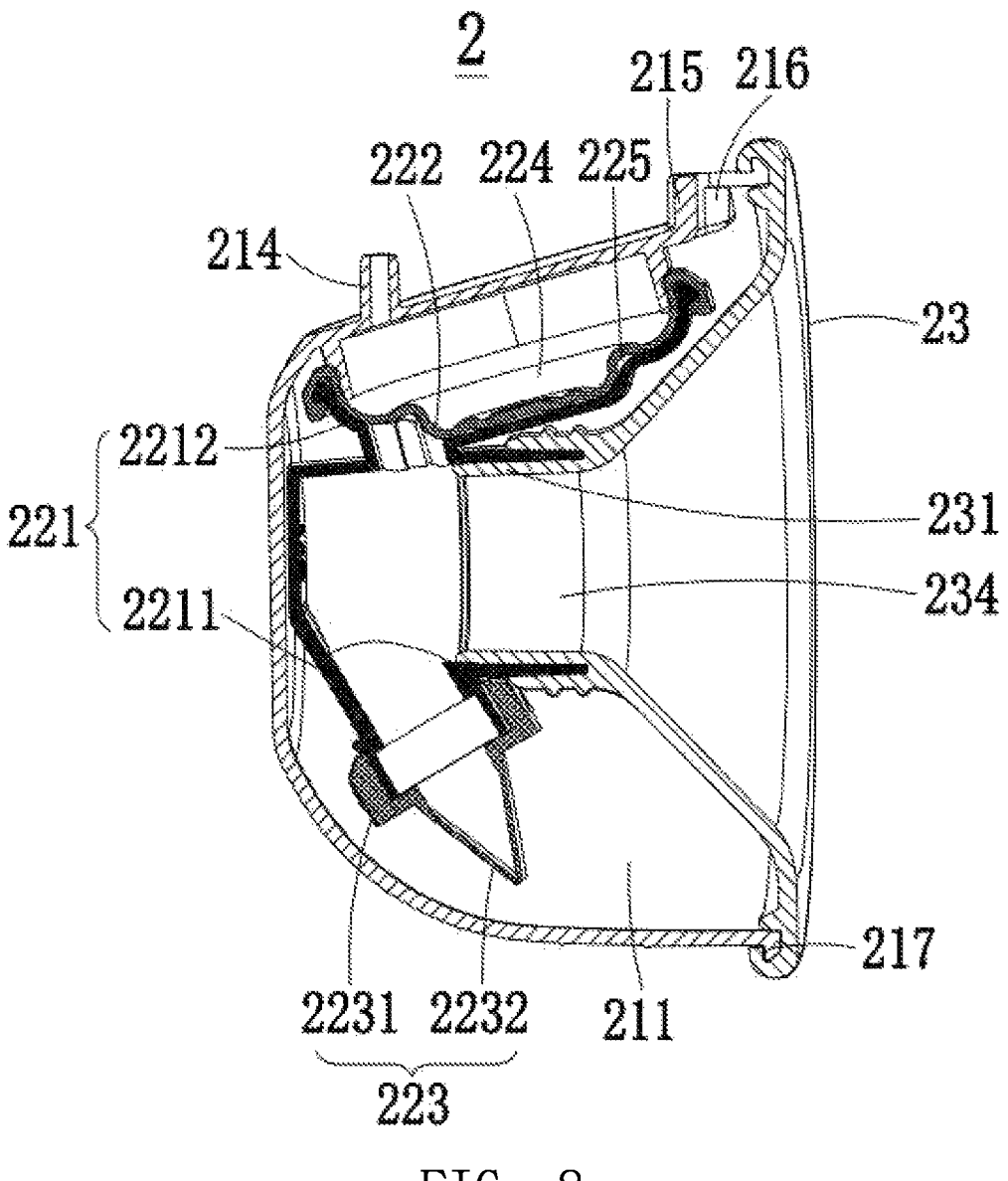
FIG. 8 is a schematic cross-sectional structural diagram of the breast pump assembly of the present disclosure.

Referring to FIGS. 7 and 8, the breast pump assembly 2 includes a storage member 21, an adapter 22 and a face cover 23. The face cover 23 is connected to the storage member 21 and the adapter 22, and the face cover 23 encapsulates the adapter 22 inside the storage member 21.

The storage member 21 is provided with an accommodating cavity 211, and the accommodating cavity 211 is used for accommodating the adapter 22, and at the same time, the accommodating cavity 211 is also used for containing the milk pumped from the mammary glands. There is no need to configure an additional bottle to receive milk, which is convenient to use.

The outer wall of the storage member 21 is provided with a capacity scale 212, which is convenient for observing the capacity of the milk contained in the accommodating cavity 211 and prompting the user whether to continue pumping milk.

The storage member 21 is provided with a second surface 213. When the storage member 21 is installed on the upper half shell 111, the second surface 213 is fitted with the first surface 1113 of the upper half shell 111, and the thickness of the second surface 213 is the same as that of the upper half shell 111. The directions are arranged at an included angle, and it can be understood that the second surface 213 is inclined with respect to the horizontal plane. The inclinations of the first surface 1113 and the second surface 213 are consistent, so that the first surface 1113 and the second surface 213 can be completely fitted together, and the upper half shell 111 supports the storage member 21 stably.

The second surface 213 is provided with a connecting post 214, the connecting post 214 protrudes from the second surface 213 and the connecting post 214 is hollow tubular. One end of the connecting post 214 is communicated with the adapter 22, and the other end of the connecting post 214 is exposed to the outside. The connecting post 214 is used to be detachably inserted into the connecting groove 151 of the three-way connector 15. When the connecting post 214 is inserted into the connecting groove 151, the pneumatic pump 13 can vacuum or pressurize the adapter 22. When the connecting column 214 is disassembled and separated from the connecting groove 151, the connecting post 214 and the connecting groove 151 can be connected to both ends of the ventilation tube 3, and the pneumatic pump 13 can still vacuum or pressurize the adapter 22. In addition, the connecting post 214 is inserted into the connecting groove 151, and can also play the role of fixing the storage member 21, so that the storage member 21 can be installed more firmly on the upper half shell 111.

The second surface 213 is further provided with a positioning flange 215, and the shape of the positioning flange 215 is adapted to the shape of the positioning groove 1114 of the upper half shell 111, so that the positioning flange 215 can be completely inserted into the positioning groove 1114.

The positioning flange 215 is provided with an insertion hole 216, and the shape of the insertion bole 216 is adapted to the shape of the insertion post 1115 in the positioning groove 1114, so that the insertion post 1115 can be mated and inserted with the insertion hole 216. When the insertion post 1115 can be mated with the insertion hole 216, the positioning flange 215 is inserted into the positioning groove 1114, so that the storage member 21 is more stably installed on the upper half shell 111. Of course, in other embodiments, the positioning groove 1114 and the insertion post 1115 of the upper half shell 111, the positioning flanges 215 and the insertion holes 216 of the storage member 21 can be interchanged, and the storage member 21 can also be connected to the upper half shell 111.

The side of the storage member 21 facing the face cover 23 is provided with an annular clip flange 217 along the circumferential direction. The clip flange 217 is used for detachably snap-fit with the face cover 23, so that the face cover 23 and the storage member 21 can be clip-fitted detachably.

The side of the storage member 21 facing away from the surface cover 23 has a third surface 218, and the third surface 218 is used to be attached to a placing surface such as a desktop. When the storage member 21 is connected to the upper half shell 111, the third surface 218 can cooperate with the bottom shell 113 to be attached to the placing surface together to support the breast pump 100 together, so that the milk stored in the storage member 21 can be placed stably.

The face cover 23 is in the shape of a funnel, and a side of the face cover 23 facing the storage member 21 has a socket 231, and the socket 231 is used for detachably plugging with the adapter 22. A sealing ring 232 is sleeved on the socket 231, and the sealing ring 232 is used to seal the gap between the socket 231 and the adapter 22 to ensure the tightness of the connection between the face cover 23 and the adapter 22.

An annular mounting groove 233 is defined on the peripheral edge of the surface cover 23 facing the storage member 21. It can be understood that, in other embodiments, the face cover 23 and the storage member 21 may also be connected in other detachable manners, such as magnetic connection, screw connection, etc., which are not limited herein. When the milk in the accommodating cavity 211 needs to be poured out, the face cover 23 can be disassembled and separated from the storage member 21. When it is necessary to pump milk, the face cover 23 can be connected to the storage member 21

The face cover 23 has a hollow liquid inlet groove 234, the liquid inlet groove 234 communicates with the adapter 22, and the end of the face cover 23 facing away from the storage member 21 is used for sticking on the breast. When the adapter 22 is evacuated, the liquid inlet groove 234 forms a negative pressure to suck the milk in the mammary glands, and the milk enters the adapter 22 through the liquid inlet groove 234.

The adapter 22 includes an adapter housing 221, an air pressure elastic member 222 and a milk release member 223. The air pressure elastic element member 222 and the milk release member 223 are both connected to the adapter housing 221.

The adapter housing 221 is connected to the storage element 21, and the pneumatic elastic element 222 is located between the adapter case 221 and the storage element 21. A first air pressure chamber 224 is formed between the air pressure elastic member 222 and the storage member 21, a second air pressure chamber 225 is formed between the air pressure elastic member 222 and the adapter housing 221, and the first air pressure chamber 224 communicates with the connecting post 214 on the storage member 21. The second air pressure chamber 225 communicates with the adapter housing 221.

The air pressure elastic member 222 is made of elastic material, and the air pressure elastic member 222 can be elastically deformed to adjust the air pressure of the first air pressure chamber 224 and the second air pressure chamber 225. When the pneumatic pump 13 evacuates the first air pressure chamber 224 through the connecting post 214, the space of the first air pressure chamber 224 gradually decreases, the air pressure elastic member 222 is elastically deformed away from the adapter housing 221, and the space of the second air pressure chamber 225 gradually decreases and the second air pressure chamber 225 forms a negative pressure on the adapter housing 221. The adapter housing 1

221 sucks the milk in the mammary glands through the face cover 23, and the milk can be stored in the milk release member 223.

When the pneumatic pump 13 inflates and pressurizes the first air pressure chamber 224 through the connecting post 214, the space of the first air pressure chamber 224 gradually increases, the air pressure elastic member 222 is elastically deformed toward the adapter housing 221, and the space of the second air pressure chamber 225 gradually increases. When the pressure decreases, the second air pressure chamber 225 pressurizes the adapter housing 221, and the adapter housing 221 drives the milk in the milk release member 223 to release the milk to the accommodating cavity 211.

The adapter housing 221 includes an air pressure housing 2211 and a tube body 2212, and the air pressure housing 2211 and the tube body 2212 are integrally formed, so that the air tightness between the air pressure housing 2211 and the tube body 2212 is good.

The air pressure housing 2211 is sealedly connected to the storage member 21, and the above-mentioned second air pressure chamber 225 is formed between the air pressure housing 2211 and the air pressure elastic member 222. The air pressure housing 2211 communicates with the tube body 2212, so that the air pressure of the second air pressure chamber 225 can be transmitted to the tube body 2212.

The shape of the air pressure housing 2211 is similar to the shape of the air pressure elastic member 222, and both are round cakes, so as to increase the air pressure change efficiency of the second air pressure chamber 225. When the air pressure elastic member 222 is deformed, the air pressure change efficiency of the second air pressure chamber 225 is high.

The side portion of the tube body 2212 is threadedly connected to the milk release member 223, and the tube body 2212 communicates with the milk release member 223. The milk sucked by the tube body 2212 through the face cover 23 can flow into the milk release member 223 for temporary storage. When the air pressure of the tube body 2212 increases, the milk in the milk release member 223 can be driven to release the milk into the accommodating cavity 211 of the storage member 21.

The milk release member 223 includes a connecting head 2231 and a one-way head 2232, and the connecting head 2231 and the one-way bead 2232 are integrally formed. The connecting head 2231 is screwed to the tube body 2212, so that the milk release member 223 is connected to the tube body 2212.

The one-way head 2232 is made of soft material, such as silicone or rubber, and one end of the one-way head 2232 facing away from the connecting head 2231 has an opening. The milk sucked by the tube body 2212 flows into the one-way head 2232 for temporary storage. When the tube body 2212 is in a negative pressure state, the opening of the one-way head 2232 is tightly closed to hold the pumped milk. When the inside of the tube body 2212 is in a pressurized state, the air pressure can drive the opening of the one-way head 2232 to open, and the milk flows into the accommodating cavity 211 through the opening. Therefore, through the cyclic vacuuming and pressurization of the pneumatic pump 13, the milk in the mammary glands can be pumped to the one-way head 2232, and then the milk is released to the accommodating cavity 211. The stored milk will gradually increase, thereby achieving the goal of the suction and storage of milk.

The technical features of the above embodiments can be combined arbitrarily. In order to make the description simple, all possible combinations of the technical features in the above embodiments are not described. However, as long as there is no contradiction in the combination of these technical features, they should be considered to be within the scope of the description in this specification.

The above examples only represent several embodiments of the present disclosure, and the descriptions thereof are more specific and detailed, but should not be construed as a limitation on the scope of the patent of the present disclosure. It should be pointed out that for those of ordinary skill in the art, without departing from the concept of the present disclosure, several deformations, replacements and improvements can also be made, and these should be included within the protection scope of the present disclosure. Therefore, the protection scope of the patent for the present disclosure should be subject to the claims.

What is claimed is:

1. A breast pump, comprising:
a wearable breast pump assembly, comprising:
    a storage member comprising: a first coupling assembly, wherein the first coupling assembly comprises at least one of an insertion hole or a positioning flange;
    a first ventilation connector;
    a face cover, having a breast holding space to hold a user's breast for pumping milk, wherein the face cover is in sealed connection to the storage member, forming a milk holding cavity between the face cover and the storage member;
    an air pressure elastic member, arranged in the milk holding cavity and being in sealed connection to an internal surface of the storage member, forming a first air pressure chamber enclosed by the internal surface of the storage member and the air pressure elastic member, wherein the first air pressure chamber is in communication with the first ventilation connector, and the internal surface occupies a majority of an area facing the air pressure elastic member in the air pressure chamber;
    an adapter housing, arranged in the milk holding cavity and being in sealed connection to the air pressure elastic member and to the face cover to receive the milk from the breast holding space; and
a base, comprising:
    a housing, comprising a second coupling assembly detachably coupled with the first coupling assembly; wherein the second coupling assembly comprises at least one of an insertion post or a positioning groove;
    a pneumatic pump, arranged in the housing to generate a negative air pressure;
    a second ventilation connector, in communication with the pneumatic pump, and being directly connected to the first ventilation connector to transmit the negative air pressure to the breast holding cavity via the first ventilation connector, the first air pressure chamber and the adapter housing.

2. The breast pump according to claim 1, wherein the second coupling assembly comprises the insertion post arranged on the housing,
the first coupling assembly comprises the insertion hole, and
the insertion post and the insertion hole are detachably engaged to each other.

3. The breast pump according to claim 2, wherein the second coupling assembly comprises the positioning groove arranged on the housing, the insertion post is arranged in the positioning groove,
the first coupling assembly comprises the positioning flange, the insertion hole is arranged in the positioning flange, and, when the insertion post is engaged to the insertion hole, the positioning flange is engaged to the positioning groove.

4. The breast pump according to claim 1, wherein the housing has a first outer surface, the wearable breast pump assembly has a second outer surface, the first outer surface is arranged at an angle to a bottom surface of the base, and the first outer surface is in contact with the outer second surface.

5. The breast pump according to claim 1, wherein the housing is provided with a movable groove that is hollow, so that a mounting cross rod is arranged on the housing, a mounting hook for fixing the base on the user's body is sleeved on the mounting cross rod and is able to rotate in the movable groove.

6. The breast pump according to claim 5, wherein the mounting hook has a first section, a second section and a third section, the first section and the third section are respectively arranged on opposite sides in a thickness direction of the second section, the first section is curved to be sleeved on the mounting cross rod, and the third section is curved to be detachably fastened to the user.

7. The breast pump according to claim 5, wherein the mounting hook comprises a first section, a second section, and a third section; and wherein the first section and the third section are curved, and are provided on opposite side of the second section in a thickness direction of the mounting hook.

8. The breast pump according to claim 1, wherein a mobile power supply is provided in the housing, and the mobile power supply is configured to supply power to the pneumatic pump.

9. The breast pump according to claim 1, wherein the first ventilation connector is along a first direction;

the breast holding space is configured to hold the user's breast from a second direction; and the first direction is different from the second direction.

\* \* \* \* \*